United States Patent
Wang et al.

(10) Patent No.: US 11,369,362 B2
(45) Date of Patent: Jun. 28, 2022

(54) FIBROCARTILAGE SUTURING DEVICE

(71) Applicant: METAL INDUSTRIES RESEARCH & DEVELOPMENT CENTRE, Kaohsiung (TW)

(72) Inventors: Chen-Chie Wang, Taipei (TW); Po-Chih Chow, Taipei (TW); Yue-Jun Wang, New Taipei (TW); Shih-Hua Huang, Kaohsiung (TW); Chih-Lung Lin, Kaohsiung (TW); Tung-Lin Tsai, Tainan (TW); Chun-Chieh Tseng, Kaohsiung (TW); Li-Wen Weng, Kaohsiung (TW)

(73) Assignee: METAL INDUSTRIES RESEARCH & DEVELOPMENT CENTRE, Kaohsiung (TW)

( * ) Notice: Subject to any disclaimer, the term of this patent is extended or adjusted under 35 U.S.C. 154(b) by 365 days.

(21) Appl. No.: 16/568,534

(22) Filed: Sep. 12, 2019

(65) Prior Publication Data
US 2020/0155138 A1    May 21, 2020

(30) Foreign Application Priority Data
Nov. 15, 2018   (TW) .................. 107140586

(51) Int. Cl.
*A61B 17/04*         (2006.01)
(52) U.S. Cl.
CPC ...... *A61B 17/0401* (2013.01); *A61B 17/0469* (2013.01); *A61B 17/0482* (2013.01); *A61B 17/0485* (2013.01); *A61B 2017/045* (2013.01); *A61B 2017/0409* (2013.01); *A61B 2017/0412* (2013.01); *A61B 2017/0429* (2013.01)

(58) Field of Classification Search
CPC ........ A61B 17/0401; A61B 2017/0412; A61B 2017/0427; A61B 2017/0437
See application file for complete search history.

(56) References Cited

U.S. PATENT DOCUMENTS 4,994,079 A * 2/1991 Genese ............... A61B 17/221
                                                 606/206
5,662,654 A * 9/1997 Thompson ......... A61B 17/0469
                                                 606/232

(Continued)

FOREIGN PATENT DOCUMENTS

WO   WO2014134102 A3   9/2014
WO   WO2016068896 A1   5/2016

*Primary Examiner* — Nicholas W Woodall
(74) *Attorney, Agent, or Firm* — Alan D. Kamrath; Karin L. Williams; Mayer & Williams PC

(57) ABSTRACT

A fibrocartilage suturing device is provided to solve the problem where the conventional procedure of the surgery is inconvenient. The fibrocartilage suturing device includes a tube assembly, a tubular member, and an anchor. The tube assembly extends through the tube assembly and includes an insertion section. The movement member is coupled with the tube assembly and includes a thrust rod extending through the tubular member. The anchor is located at one end of the thrust rod and includes a body and at least two wings connected to the body is able to be folded and unfolded relative to the body. The body of the anchor is connected to an end of a thread. Another end of the thread is connected to the tubular member.

8 Claims, 8 Drawing Sheets

(56) References Cited

U.S. PATENT DOCUMENTS

2002/0161382 A1\* 10/2002 Neisz ................ A61B 17/0487
                                                    606/151
2008/0287988 A1\* 11/2008 Smith ................ A61B 17/0469
                                                    606/216

\* cited by examiner

FIBROCARTILAGE SUTURING DEVICE

The application claims the benefit of Taiwan application serial No. 107140586, filed on Nov. 15, 2018, and the entire contents of which are incorporated herein by reference.

BACKGROUND OF THE INVENTION

1. Field of the Invention

The present invention relates to a medical instrument and, more particularly, a fibrocartilage suturing device used in suture surgery of a broken metatarsal.

2. Description of the Related Art

In the present society, breaking of metatarsal often occurs in people while wearing high heeled shoes for a long period of time. Metatarsal is a fibrocartilage below the joint of the metatarsal and the bones of toes, which functions in stabilizing the toes. The fibrocartilage tends to be torn or peeled under a state of pulling force for a long period of time, causing the bones of toes to be unstable. The complication of tilted toes occurs when the back muscle is pulled. In early years, many patients would bear the pain without going to see a doctor. In recent years, more patients go to see a doctor and consult the doctors for therapy, allowing medical records of injury of broken metatarsal to be created.

However, there is no suturing device used specifically for fibrocartilage in the suture surgery of the broken metatarsal at present. For reasons that success of suturing metatarsal is not easy to be archived due to different device complications, suturing of the metatarsal must be proceeded in a small space of fibrocartilage with a suture needle during suture surgery of the metatarsal, resulting in inconvenient surgery. It may result not only in a greater time required for the surgery, but also may increase the risk, difficulty and complexity of the surgery.

Based on the above, it is necessary to improve the conventional suturing device used in suture surgery of a broken metatarsal.

SUMMARY OF THE INVENTION

To solve the problems mentioned above, the purpose of the present invention is to provide a fibrocartilage suturing device which allows an anchor to be positioned steadily without turning or moving back easily. Moreover, the thread positioned within the fibrocartilage suturing device after tying before the surgery improves the convenience of the surgery.

Another purpose of the present invention is to provide a fibrocartilage suturing device which avoids the deformation of the anchor when subject to pressure.

A further purpose of the present invention is to provide a fibrocartilage suturing device which avoids causing a foreign body sensation after being implanted into a patient's body.

Still yet a further purpose of the present invention is to provide a fibrocartilage suturing device which has a simple structure to reduce the manufacturing cost.

The direction terms or similar terms thereof described hereinafter of the present invention, such as "front", "rear", "left", "right", "up (top)", "low (bottom)", "inner", "outer", "lateral" etc. should be understood that these terms have reference only to the structure shown in the drawings as it would appear to a person viewing the drawings, and are utilized only to facilitate describing the invention, rather than limiting the scope of the present invention.

A fibrocartilage suturing device of the present invention includes a tube assembly, a tubular member, a movement member and an anchor. The tube assembly extends through the tube assembly and includes an insertion section. The movement member is coupled with the tube assembly and includes a thrust rod extending through the tubular member. The anchor is located at one end of the thrust rod and includes a body and at least two wings are connected to the body. Each of the at least two wings is able to be folded and unfolded relative to the body. The body of the anchor is connected to an end of a thread, and another end of the thread is connected to the tubular member.

Accordingly, the fibrocartilage suturing device of the present invention the at least two wings may meet the fibrocartilage, allowing the anchor to be positioned steadily without turning or moving back easily. Moreover, the thread positioned within the fibrocartilage suturing device after tying before the surgery decreases the difficulty of suturing due to the small limitation. Accordingly, the operation convenience during the surgery may be increased followed by enhancing overall surgery effect.

In one embodiment, the tube assembly has a first tube unit and a second tube unit, and wherein a first coupling portion of the first tube unit is connected to a second coupling portion of the second tube unit. As such, it may ensure the effect of reducing manufacturing costs.

In one embodiment, the tube assembly has a tube portion at the second tube unit. The insertion section of the tubular member is exposed outside of the tube portion. As such, it may ensure the effect of enhancing the convenience of surgery.

In one embodiment, the tubular member has a thread hole and a wire-fixing portion, wherein the thread passes through the thread hole within the tube assembly, and wherein the thread is exposed partially outside of the tubular member and is connected to the wire-fixing portion. As such, it may ensure the effect of enhancing the convenience of surgery.

In one embodiment, the movement member has a handgrip connected to the thrust rod, wherein the handgrip has two groove portions respectively connected to each of two guiding rails of the tube assembly, and wherein a thickness of the handgrip reduces from one end to another end thereof. As such, it may ensure the effect of enhancing the convenience of surgery.

In one embodiment, an angle is formed between each of the at least two wings, and is smaller than 180°. As such, it may ensure the effect of meeting each of the at least two wings to the fibrocartilage.

In one embodiment, an outer surface of the body has at least two reduced portions respectively corresponding to the at least two wings. As such, as each of the at least two wings is in an unfolded state and attached to the at least two reduced portions, it may ensure the effect of avoiding the anchor from deformation when pressed.

In one embodiment, as each of the at least two wings is in an unfolded state relative to the body, an angle is formed between each of the at least two wings and a central axis of the anchor, and wherein 15°≤angle (α)≤90°. As such, it may ensure the effect of each of the at least two wings of the anchor to be meet steady to the fibrocartilage.

In one embodiment, the body is integrally formed with the at least two wings. As such, it provides the effect of enhancing the structural strength of the anchor.

In one embodiment, the body is in an arc shape. As such, it may provide the effect of avoiding causing a foreign body sensation after being implanted into a patient's body.

BRIEF DESCRIPTION OF THE DRAWINGS

The present invention will become more fully understood from the detailed description given hereinafter and the accompanying drawings which are given by way of illustration only, and thus are not limitative of the present invention, and wherein.

DETAILED DESCRIPTION OF THE INVENTION

Figure 1:
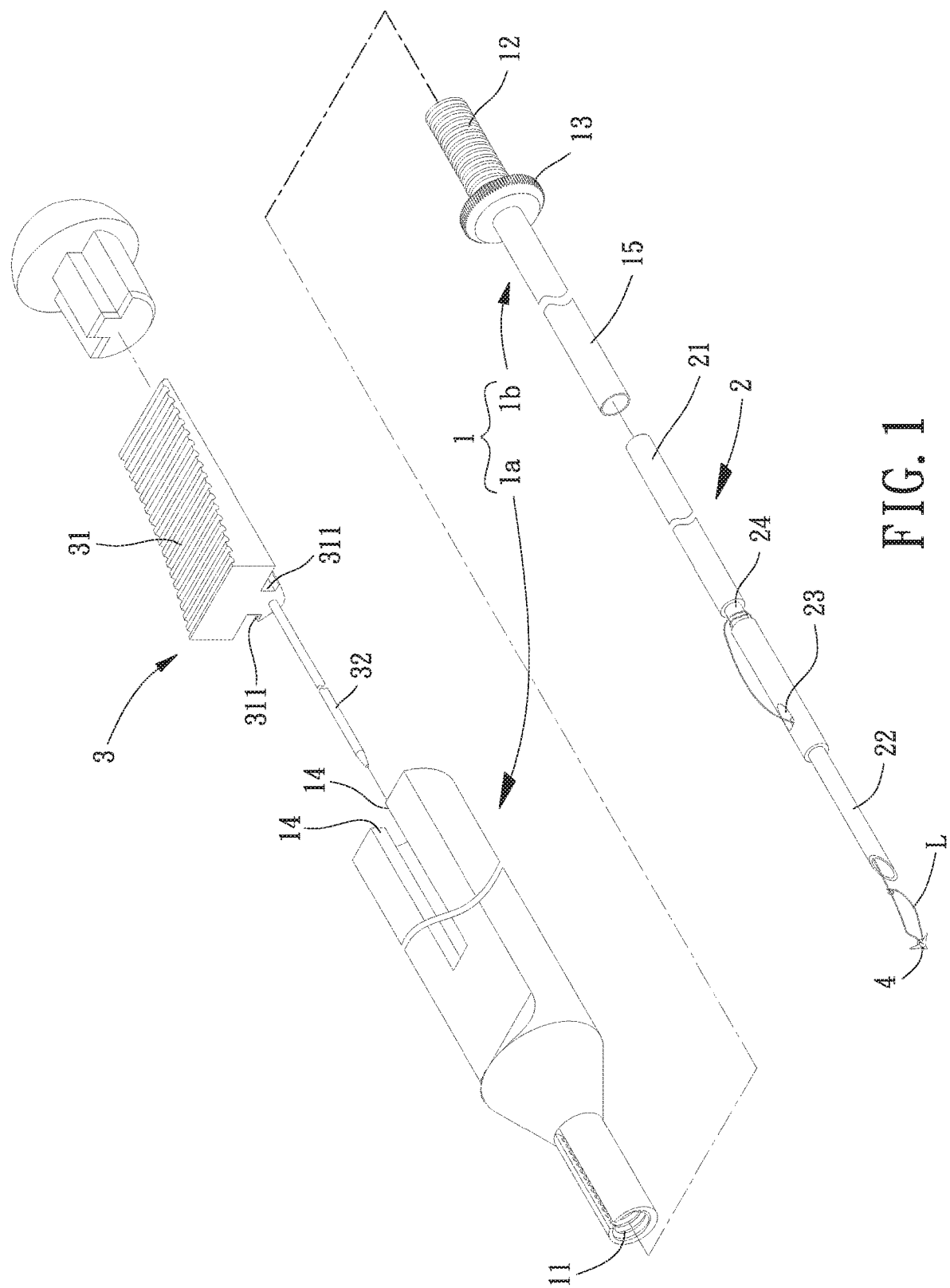
FIG. 1 is a stereoscopic exploded view of a fibrocartilage suturing device according to a preferred embodiment of the present invention.

Referring to FIG. 1, a preferred embodiment of the present invention comprises a tube assembly 1, a tubular member 2, a movement member 3 and an anchor 4. The tubular member 2 and the movement member 3 are connected to the tube assembly 1. The anchor 4 is at one end of the movement member 3.

Figure 4:
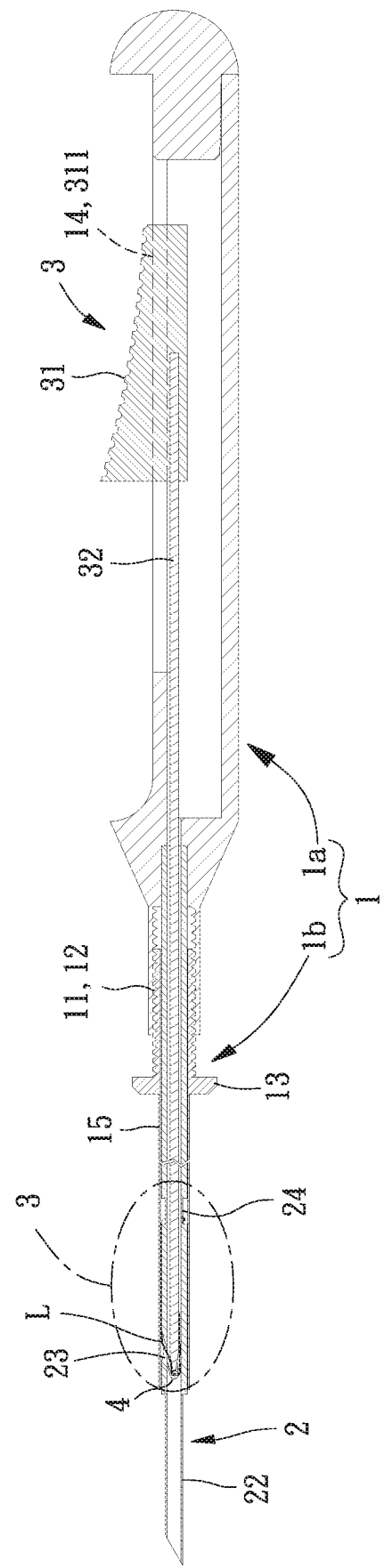
FIG. 4 is an assembly cross-sectional view of a fibrocartilage suturing device according to a preferred embodiment of the present invention.
Figure 6:
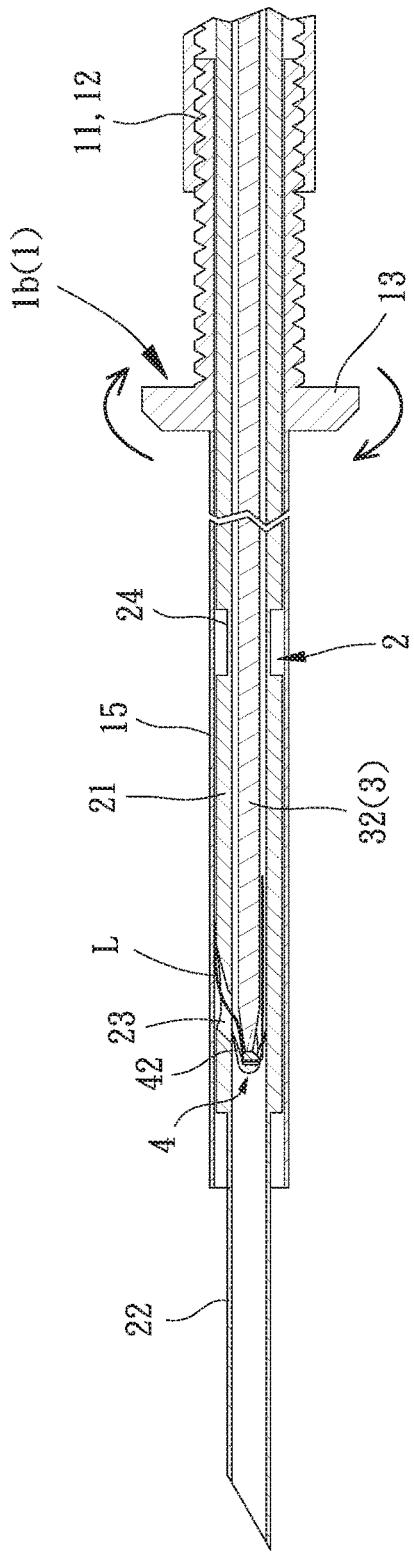
FIG. 6 shows an action condition view of a turning adjusted portion as shown in FIG. 4.

Referring to FIGS. 1, 4 and 6, the tube assembly 1 includes a first tube unit 1a and a second tube unit 1b connected to the first tube unit 1a. The first tube unit 1a may have a first coupling portion 11 adjacent to one end of the second tube unit 1b. The second tube unit 1b may have a second coupling portion 12 adjacent to one end of the first tube unit 1a. The second coupling portion 12 and the first coupling portion 11 may have matched structures, allowing the second coupling portion 12 to be coupled with the first coupling portion 11. The structures of the second coupling portion 12 and the first coupling portion 11 are not limited in the present invention. In the present embodiment, an inner thread was formed in the first coupling portion 11 and an outer thread was formed in the second coupling portion 12, allowing the simple structures of the second coupling portion 12 and the first coupling portion 11 to be directly threaded with each other. The second tube unit 1b may move relative to the first tube unit 1a by turning an adjustment portion 13 adjacent to the second coupling portion 12, thereby adjusting the length of the tube assembly 1.

Moreover, the tube assembly 1 may have two guiding rails 14 on a surface of the first tube unit 1a and at one end of the first tube unit 1a away from the first coupling portion 11. The tube assembly 1 may further have a tube portion 15 on the second tube unit 1b and at one end of the second tube unit 1b away from the second coupling portion 12, allowing the adjustment portion 13 to be connected between the tube portion 15 and the second coupling portion 12.

The tubular member 2 extends through the tube assembly 1. The tubular member 2 has an engagement member 21 and an insertion section 22 opposite to the engagement member 21. The engagement member 21 may be press fit inside of the first tube unit 1a of the tube assembly 1. The insertion section 22 was exposed outside of the tube portion 15 of the second tube unit 1b. Specifically, the tubular member 2 may further have a thread hole 23 and a wire-fixing portion 24. The thread hole 23 and the wire-fixing portion 24 are located between the engagement member 21 and the insertion section 22. The thread hole 23 was closer to the insertion section 22 and the wire-fixing portion 24 was closer to the engagement member 21. The structure of the wire-fixing portion 24 is not limited in the present invention. In the present embodiment, the wire-fixing portion 24 forms from the difference in outer diameters of the tubular member 2.

Figure 7:
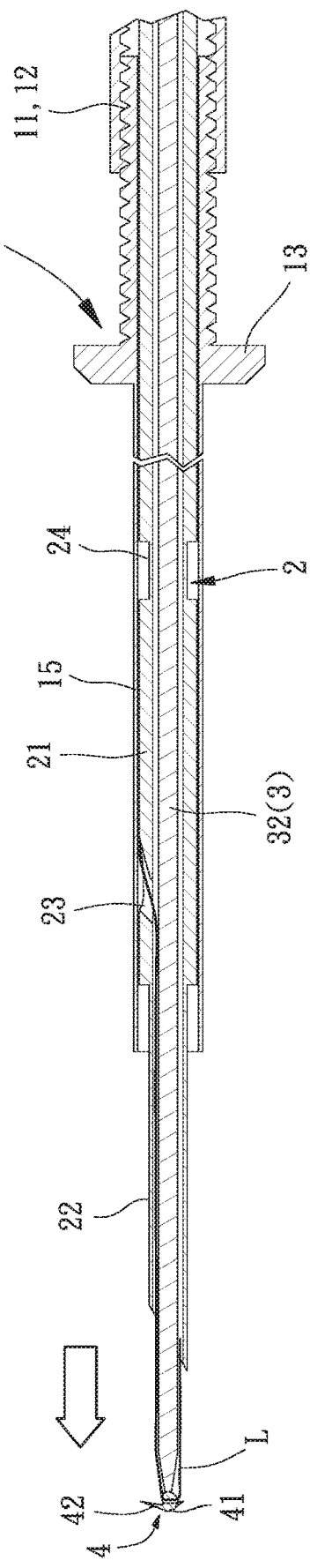
FIG. 7 shows an action condition view of a thrust rod pulled exposed outside of the tubular member as shown in FIG. 4.
Figure 8:
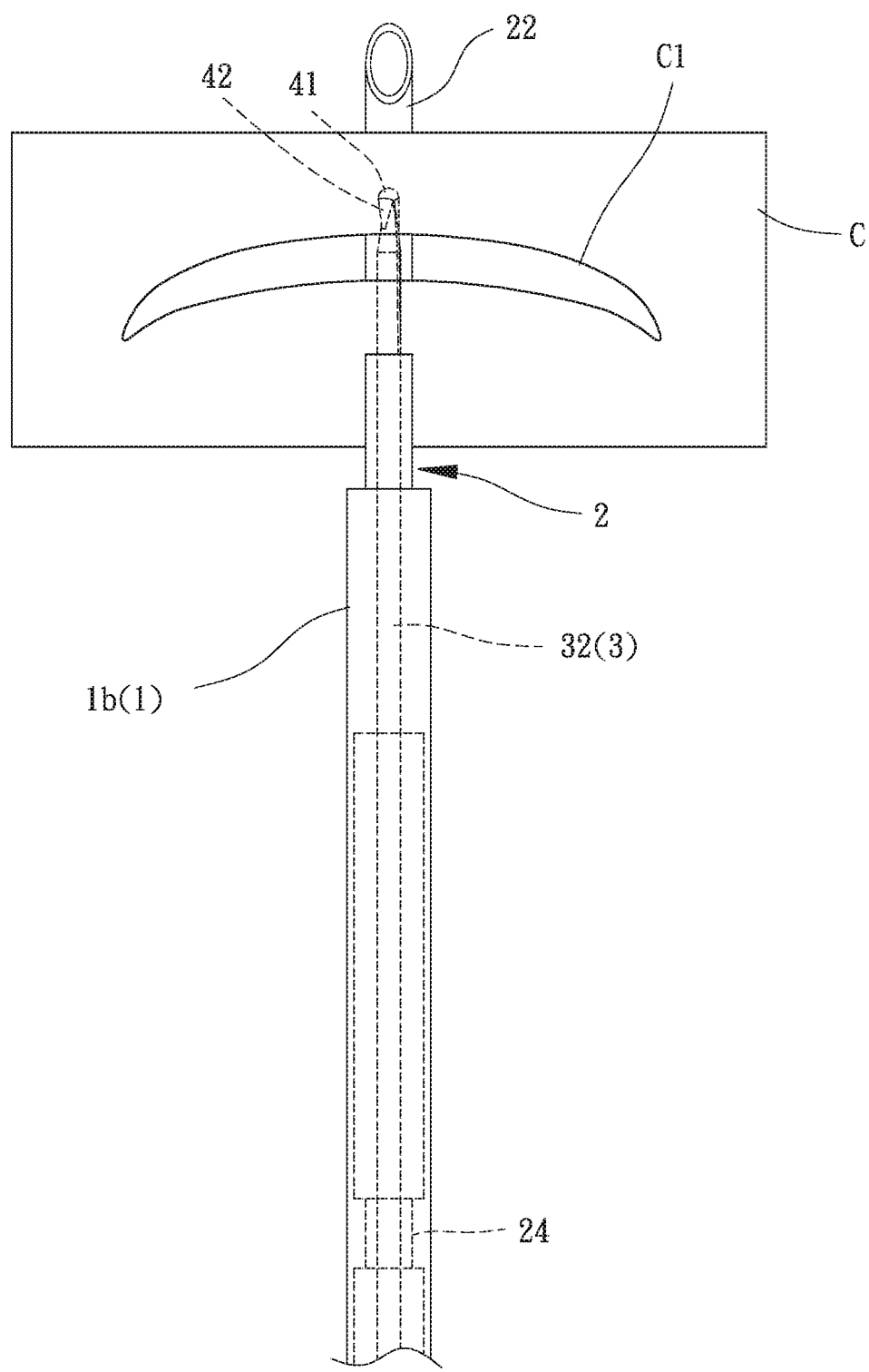
FIG. 8 is an action condition view of a fibrocartilage suturing device used during surgery according to a preferred embodiment of the present invention.

Referring to FIGS. 1, 4 and 7, the movement member 3 has a handgrip 31 and a thrust rod 32 connected to the handgrip 31 and extending through the tubular member 2. The thrust rod 32 and the handgrip 31 may be two independent parts that are connected to each other, or may be integrally formed with each other to enhance the structural strength of the movement member 3. Two groove portions 311 of the handgrip 31 may respectively connect to the two guiding rails 14, allowing the handgrip 31 to move relatively to the tube assembly 1. The thickness of the handgrip 31 preferably reduces from one end to another end thereof to provide a convenient use for the operator. The handgrip 31 was pulled and moved toward the insertion section 22 by the operator, allowing the thrust rod 32 to also move toward the insertion section 22 and to expose outside the insertion section 22.

Figure 2:
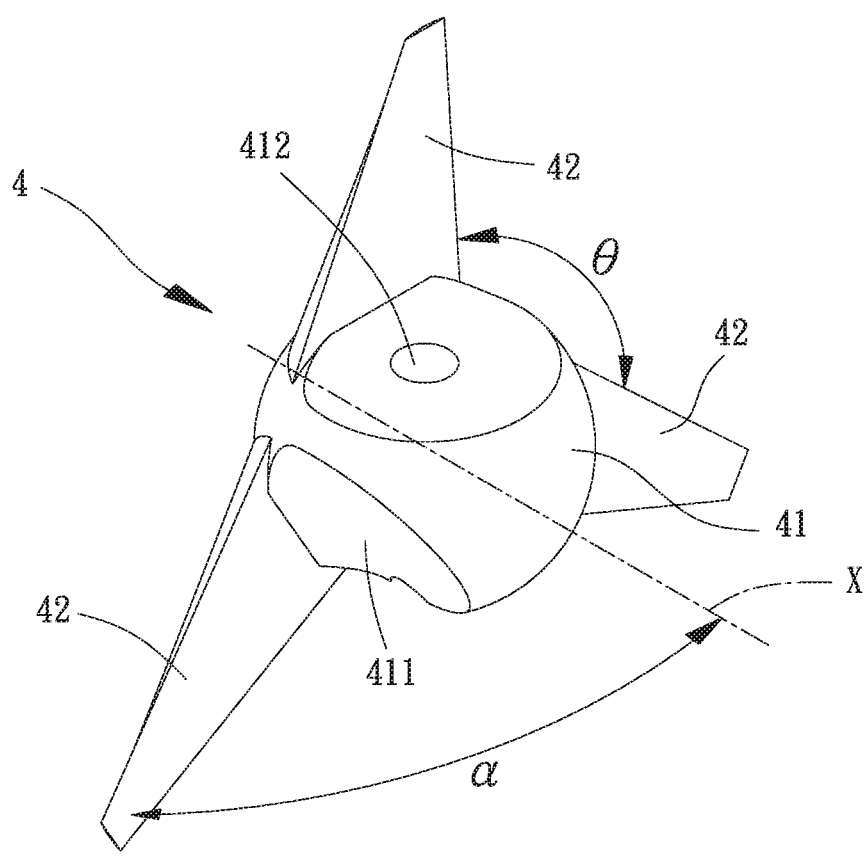
FIG. 2 is a stereoscopic view of an anchor in a folded state according to a preferred embodiment of the present invention.
Figure 3:
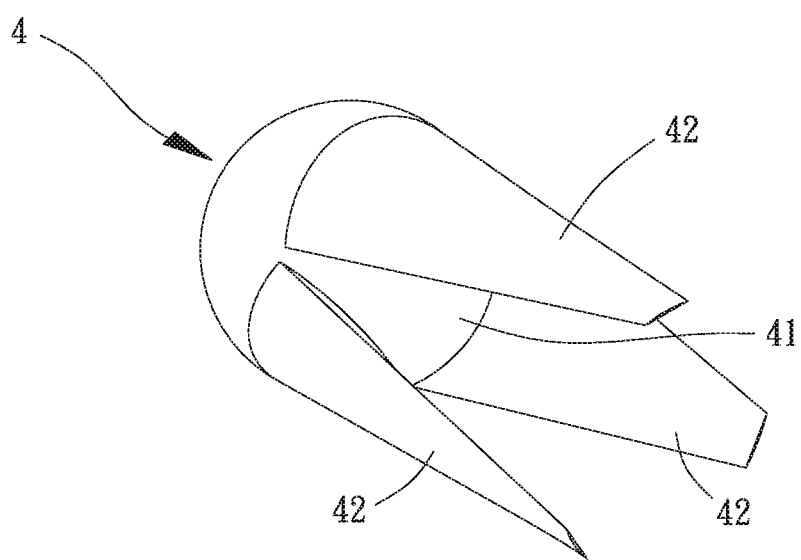
FIG. 3 is a stereoscopic view of an anchor in an unfolded state according to a preferred embodiment of the present invention.

Referring to FIGS. 1, 2 and 3, the anchor 4 was positioned in the tubular member 2 and includes a body 41 and at least two wings 42 connected to the body 41. The number of the wings 41 is preferred three expanding over the body 41, with an angle θ formed between each of the at least two wings 42. The angle θ was smaller than 180°. Preferably, the body 41 is integrally formed with the at least two wings 31 to enhance the structural strength of the anchor 4.

Particularly, the anchor 4 was made of biodegradable material such as polycaprolactone (PCL), polyethylene glycol (PEG), or poly(lactic-co-glycolic acid) (PLGA). Adjusting the temperature and injection temperature of the biodegradable material allows the anchor 4 to possess the character of a shape memory. As shown in FIG. 3, although the at least two wings 42 is pressed by a force or deforms due to the space limitation, the at least two wings 42 can be in a folded state relative to the body 41. As shown in FIG. 2, as soon as the tierce is removed, the at least two wings 42 can immediately return to an unfolded state relative to the body 41. Preferably, as each of the at least two wings 42 was in an unfolded state relative to the body 41, an angle α formed between each of the at least two wings 42 and a central axis X of the anchor 4 was 15°≤angle (α)≤90°. Preferably, an outer surface of the body 41 may have at least two reduced portions 411 corresponding to the at least two wings 42, respectively. This allows the at least two wings 42 to attach to the at least two reduced portions 411 when the at least two wings 42 were in a folded state, avoiding the anchor 4 from deformation when pressed.

Figure 5:
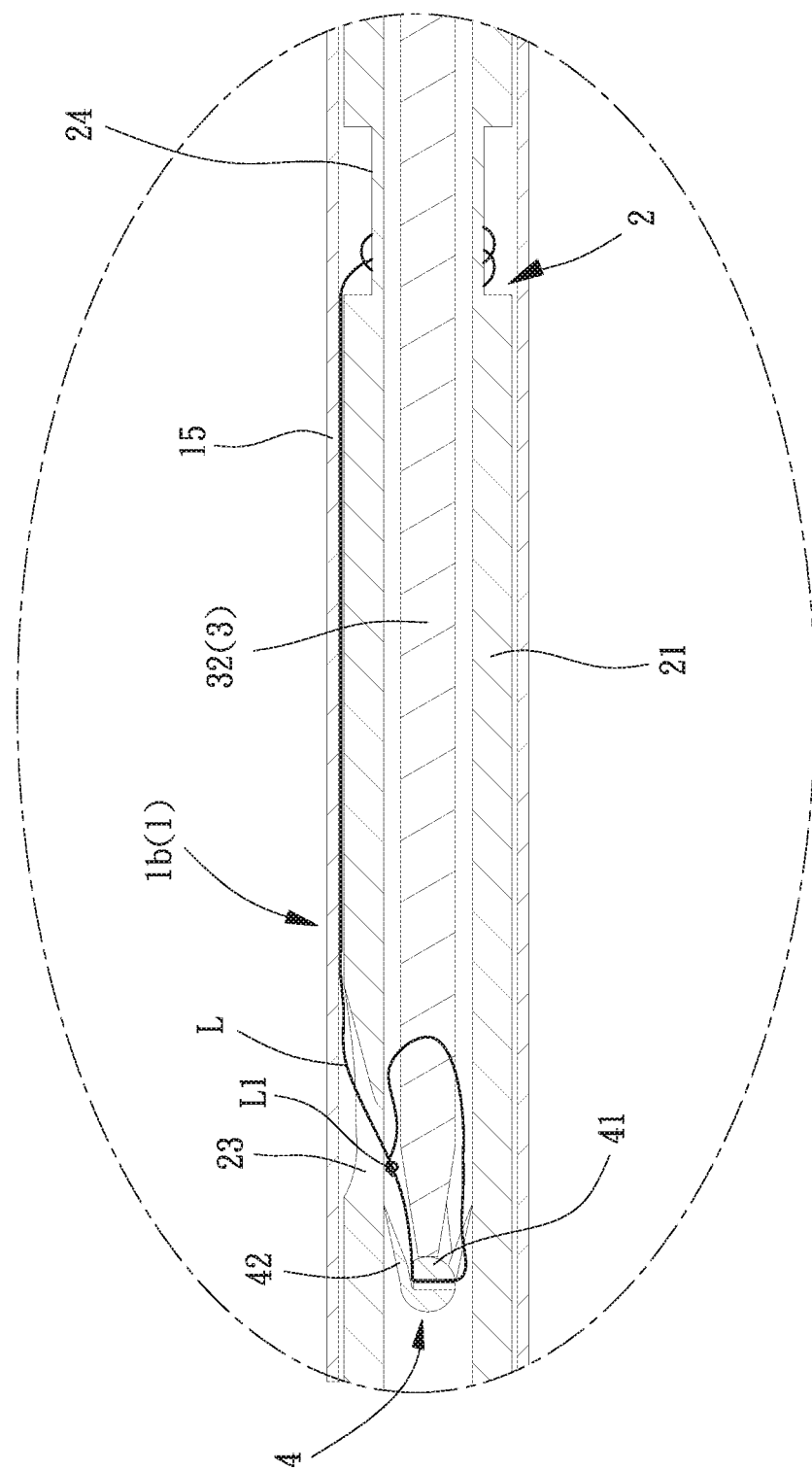
FIG. 5 is a partial, enlarged view of A as shown in FIG. 4.

Referring to FIGS. 1, 2 and 5, the shape of the body 41 is not limited in the present invention. In the present embodiment, the body 41 was in an arc shape to avoid causing a foreign body sensation after implanting into a patient's body. Specifically, the body 41 may connect to a thread L. In the present embodiment, the thread L was passed through a through-hole 412 of the body 41 and then is connected to the body 41. A knot L1 of the thread L was inside the tubular member 2, and the thread L passes through the thread hole 23 within the tubular member 2, exposing the thread L partially outside the tubular member 2 and connected to the wire-fixing portion 24. This positions the anchor 4 at one end of the thrust rod 32 of the movement member 3. As such, when the anchor 4 is in the tubular member 2, the at least two wings 42 of the anchor 4 were in a folded state limited by the inner space of the insertion section 22. The at least two wings 42 were in an unfolded state when the anchor 4 was pulled out of the insertion section 22 by the thrust rod 32.

Referring to FIGS. 6, 7, 8 and 9, based on the structure mentioned above, before operating the fibrocartilage suturing device, the operator may turn the adjustment portion 13 to move the second tube unit 1b relative to the first tube unit 1a to thereby adjust the length of the tube assembly 1 and consequently adjust the length of the insertion section 22 exposed out of the tube portion 15. Accordingly, during the surgery, the insertion section 22 was inserted into one side of the fibrocartilage C and passed through a crack C1 of the fibrocartilage C, and then threaded out of the other side of the fibrocartilage C. At this moment, the handgrip 31 moves toward the insertion section 22, driving the thrust rod 32 to move toward the insertion section 22. It allows the anchor 4 to be pulled outside of the insertion section 22 by the thrust rod 32, thus unfolding the at least two wings 42.

Figure 9:
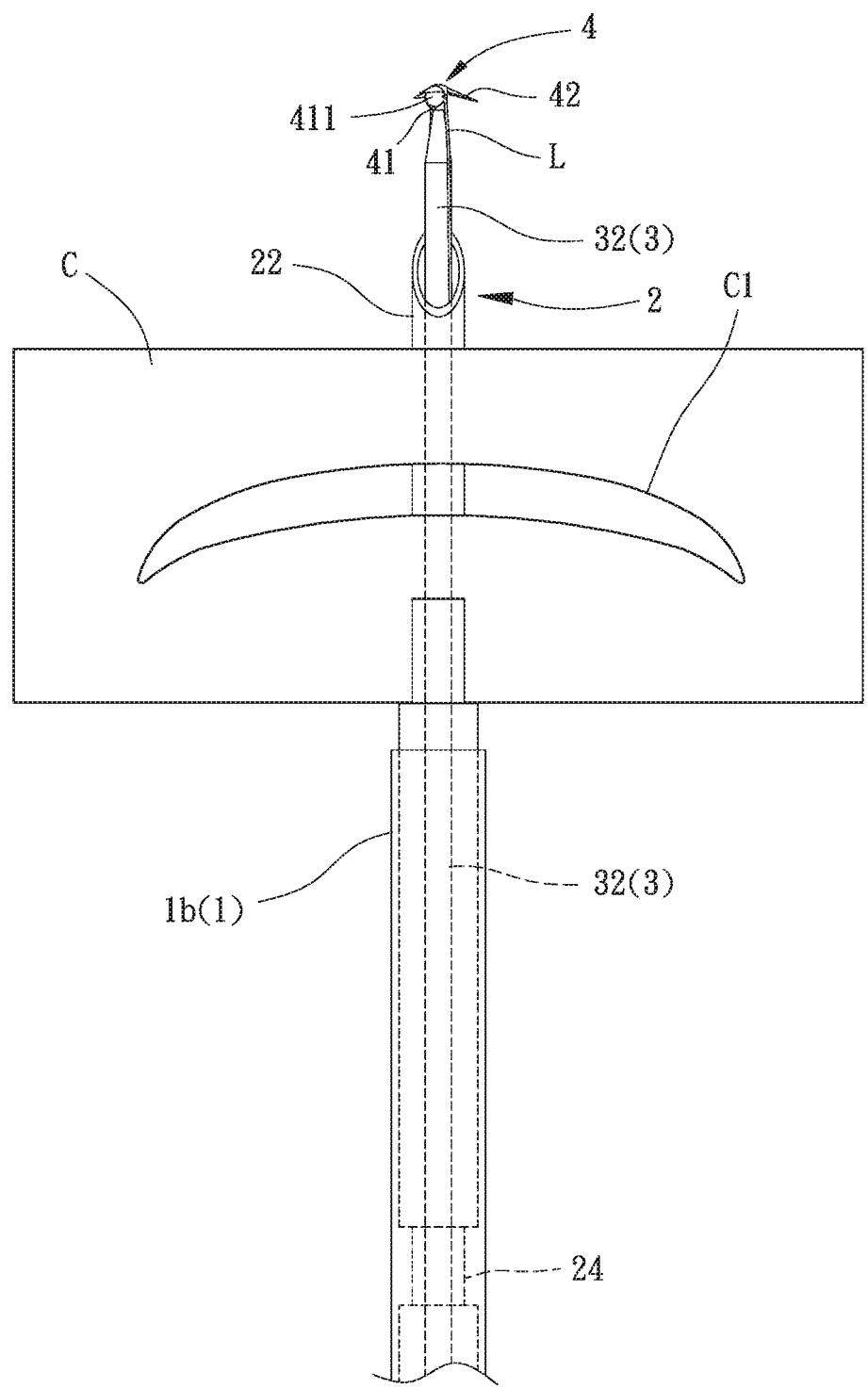
FIG. 9 shows an action condition view of FIG. 8.
Figure 10:
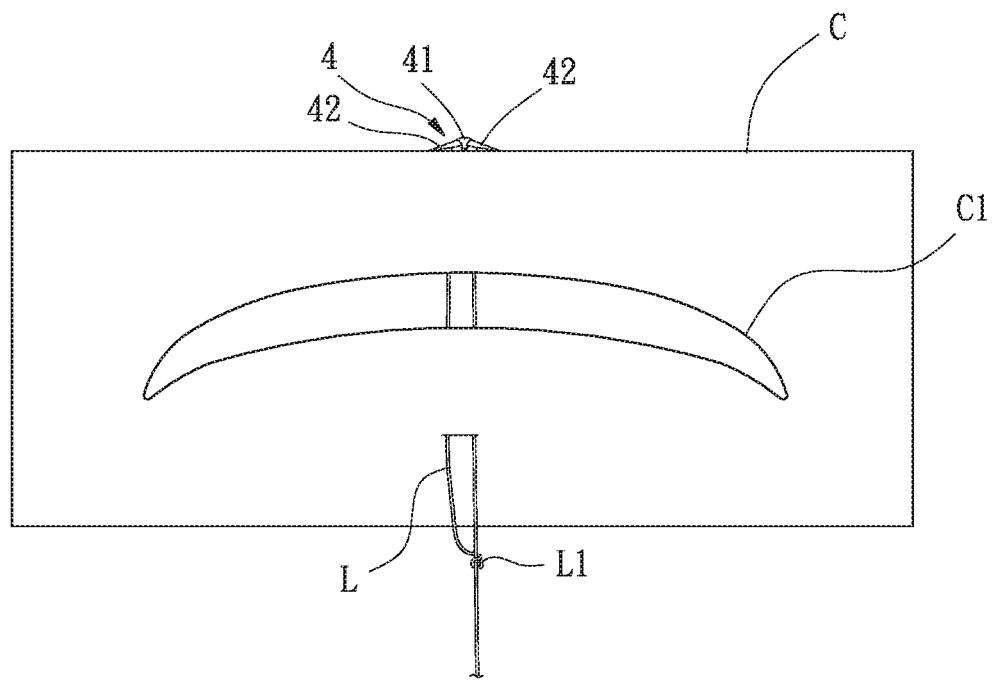
FIG. 10 is a plane view of an anchor attached to the fibrocartilage according to a preferred embodiment of the present invention.
Figure 11:
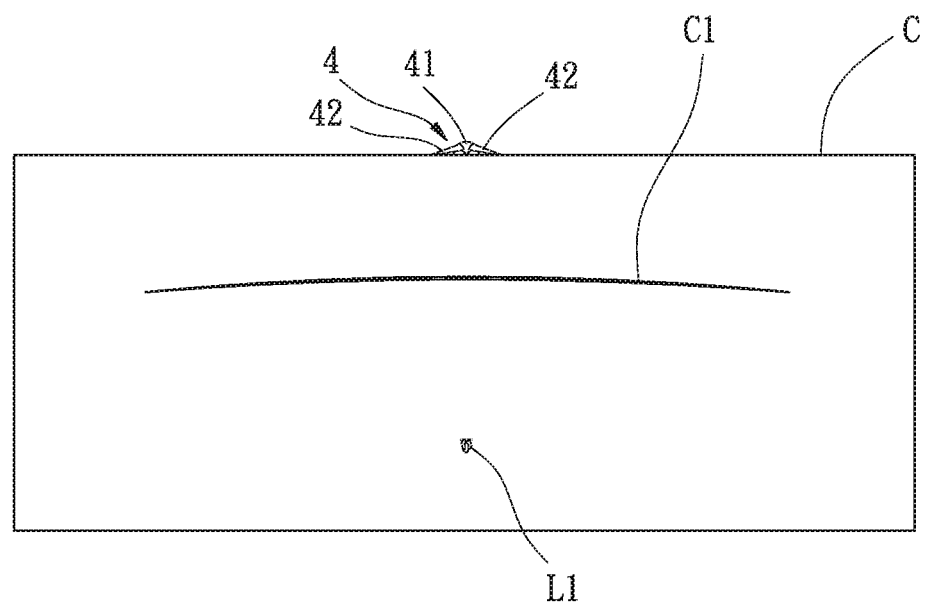
FIG. 11 is a plane view of a crack in a closed state as shown in FIG. 10.

Referring to FIGS. 9, 10 and 11, the tube assembly 1 was moved away from the anchor 4 until the at least two wings 42 of the anchor 4 abuts the fibrocartilage C, allowing the anchor 4 to be positioned at the other side of the fibrocartilage C. The knot L1 of the thread L was fixed at a proper position of the fibrocartilage C, allowing the crack C1 of the fibrocartilage C to be properly closed. The thread L was cut at one side of the fibrocartilage C to remove the fibrocartilage C of the present embodiment.

Based on the above, according to the fibrocartilage C of the present invention, the at least two wings may abut the fibrocartilage C. This allows the anchor 4 to be stably positioned at the fibrocartilage C without turning or moving back. The knot L1 of the thread L is positioned at a proper site of the fibrocartilage C, allowing the crack C1 of the fibrocartilage C to be properly closed. Moreover, the thread positioned within the fibrocartilage suturing device after tying before the surgery decreases the difficulty of suturing resulting from the small space of the fibrocartilage. Accordingly, the fibrocartilage C of the present invention provides the effects of enhancing the convenience of operation and the efficiency of the whole surgery.

It is worth mentioning that the terms "connecting", "coupling" or "assembling" or similar terms thereof mainly refer to the components that can be detached from each other without breakage, or the components that become undetached after interconnection. This includes the components having screws screwed with each other, the components connected With each other with a tape or a velcro band, the components tied with each other by a thread, the components binding each other by a magnetic force, the components binding together with an adhesive or by welding. A person of ordinary skill in the art may choose one of the above according to the materials of components to be interconnected or the requirement in assembly. Thus, the present invention is not limited to the aforementioned "connecting", "coupling" or "assembling" disclosed in the above embodiments.

Although the invention has been described in detail with reference to its presently preferable embodiments, it will be understood by one of ordinary skill in the art that various modifications can be made without departing from the spirit and the scope of the invention, as set forth in the appended claims

What is claimed is:

1. A fibrocartilage suturing device, comprising:
a tube assembly (1) having a first tube unit (1a) and a second tube unit (1b) wherein a first coupling portion (11) of the first tube unit (1a) is directly threaded with a second coupling portion (12) of the second tube unit (1b), wherein the tube assembly (1) has a tube portion (15) at the second tube unit (1b);
a tubular member (2) extending through the tube assembly (1) and including an insertion section (22);
a movement member (3) coupled with the tube assembly (1) and including a thrust rod (32) extending through the tubular member (2); and
an anchor (4) located at one end of the thrust rod (32) and including a body (41) and at least two wings (42) connected to the body (41), wherein each of the at least two wings (42) is able to be folded and unfolded relatively to the body (41), and wherein the body (41) of the anchor (4) is connected to an end of a thread (L), and another end of the thread (L) is connected to the tubular member (2);
wherein by turning the second tube unit (1b), the insertion section (22) of the tubular member (2) has an adjustable length exposed outside of the tube portion (15).

2. The fibrocartilage suturing device as claimed in claim 1, wherein the tubular member (2) has a thread hole (23) and a wire-fixing portion (24), wherein the thread (L) passes through the thread hole (23) within the tubular member (2), and wherein the thread (L) is exposed partially outside of the tubular member (2) and is connected to the wire-fixing portion (24).

3. The fibrocartilage suturing device as claimed in claim 1, wherein the movement member (3) has a handgrip (31) connected to the thrust rod (32), wherein the handgrip (31) has two groove portions (311) respectively connected to two guiding rails (14) of the tube assembly (1), and wherein a thickness of the handgrip (31) reduces from one end to another end thereof.

4. The fibrocartilage suturing device as claimed in claim 1, wherein an angle (θ) is formed between each of the at least two wings (42) and is smaller than 180°.

5. The fibrocartilage suturing device as claimed in claim 1, wherein an outer surface of the body (41) has at least two reduced portions (411) respectively corresponding to the at least two wings (42).

6. The fibrocartilage suturing device as claimed in claim 1, wherein as each of the at least two wings (42) is in an unfolded state relative to the body (41), an angle (α) is formed between each of the at least two wings (42) and a central axis (X) of the anchor (4), and wherein 15°≤angle (α)≤90°.

7. The fibrocartilage suturing device as claimed in claim 6, wherein the body (41) is integrally formed with the at least two wings (42).

8. The fibrocartilage suturing device as claimed in claim 6, wherein the body (41) is in an arc shape.

\* \* \* \* \*